(12) United States Patent
Dornblaser et al.

(10) Patent No.: US 8,269,190 B2
(45) Date of Patent: Sep. 18, 2012

(54) METHOD AND SYSTEM FOR ACHIEVING OPTIMAL UV WATER DISINFECTION

(75) Inventors: Gerald Dornblaser, Colmar, PA (US); Dennis Downie, Tamworth (GB); Jeremy Meier, Tamworth (GB); Per Olov Risman, Härryda (SE)

(73) Assignee: Severn Trent Water Purification, Inc., Colmar, PA (US)

( * ) Notice: Subject to any disclaimer, the term of this patent is extended or adjusted under 35 U.S.C. 154(b) by 111 days.

(21) Appl. No.: 12/879,668

(22) Filed: Sep. 10, 2010

(65) Prior Publication Data
US 2012/0061592 A1   Mar. 15, 2012

(51) Int. Cl.
*H01J 37/20* (2006.01)
(52) U.S. Cl. ......... 250/455.11; 250/453.11; 250/454.11; 250/504 R
(58) Field of Classification Search ........... 250/453.11–455.11, 504 R
See application file for complete search history.

(56) References Cited

U.S. PATENT DOCUMENTS

| | | |
|---|---|---|
| 3,514,604 A | 5/1970 | Grojean |
| 3,911,318 A | 10/1975 | Spero et al. |
| 4,103,167 A | 7/1978 | Ellner |
| 4,366,125 A | 12/1982 | Kodera et al. |
| 4,367,410 A | 1/1983 | Wood |
| 4,498,029 A | 2/1985 | Yoshizawa et al. |
| 4,507,587 A | 3/1985 | Wood et al. |
| 4,614,514 A | 9/1986 | Carr et al. |
| 4,673,846 A | 6/1987 | Yoshizawa et al. |
| 4,728,368 A | 3/1988 | Pedziwiatr |
| 4,757,921 A | 7/1988 | Snowball |
| 4,800,284 A | 1/1989 | Grossman et al. |
| 4,839,524 A | 6/1989 | Grossman et al. |
| 4,897,246 A | 1/1990 | Peterson |
| 4,933,602 A | 6/1990 | Ono et al. |
| 4,988,922 A | 1/1991 | Shoda et al. |
| 4,990,789 A | 2/1991 | Uesaki |
| 5,053,682 A | 10/1991 | Shoda et al. |
| 5,115,168 A | 5/1992 | Shoda et al. |
| 5,144,144 A | 9/1992 | Borovsky |
| 5,153,406 A * | 10/1992 | Smith .................. 219/121.43 |
| 5,166,528 A | 11/1992 | Le Vay |
| 5,209,902 A | 5/1993 | Matthews et al. |
| 5,320,749 A | 6/1994 | Mullen |
| 5,614,151 A * | 3/1997 | LeVay et al. .................. 422/24 |
| 6,028,315 A | 2/2000 | Bailey et al. |

(Continued)

FOREIGN PATENT DOCUMENTS

AU   2003277761   7/2004

(Continued)

OTHER PUBLICATIONS

International Search Report and Written Opinion of the International Searching Authority dated Dec. 3, 2010 for co-pending PCT patent application No. PCT/US10/02631.

*Primary Examiner* — Michael Maskell
(74) *Attorney, Agent, or Firm* — D'Ambrosio & Menon, PLLC

(57) ABSTRACT

Methods and systems are provided for enhancing the ultraviolet output of a water disinfection apparatus by: (i) maintaining the source of the UV radiation at a stable operating temperature and, (ii) facilitating an efficient transfer of microwave energy to the source of the UV radiation.

27 Claims, 6 Drawing Sheets

U.S. PATENT DOCUMENTS

| | | |
|---|---|---|
| 6,080,270 A | 6/2000 | Tabrez et al. |
| 6,087,783 A | 7/2000 | Bushnell et al. |
| 6,135,838 A | 10/2000 | Wang |
| 6,165,526 A | 12/2000 | Newman |
| 6,348,669 B1 | 2/2002 | Rudd Little et al. |
| 6,468,433 B1 | 10/2002 | Tribelski |
| 6,500,387 B1 | 12/2002 | Bigelow |
| 6,507,030 B1 | 1/2003 | Briggs et al. |
| 6,610,990 B1 | 8/2003 | Moruzzi |
| 6,693,382 B2 | 2/2004 | Little et al. |
| 6,841,790 B1 | 1/2005 | Phillips et al. |
| 6,856,093 B2 | 2/2005 | Little et al. |
| 7,081,636 B2 | 7/2006 | Moruzzi |
| 7,566,890 B2 * | 7/2009 | Briggs et al. ............... 250/504 R |
| 7,615,160 B2 * | 11/2009 | Collins et al. ............ 210/748.11 |
| 7,794,673 B2 * | 9/2010 | Lucas et al. ................ 422/186.3 |
| 2001/0047964 A1 | 12/2001 | Matherly et al. |
| 2003/0038247 A1 | 2/2003 | Schweitzer et al. |
| 2003/0122092 A1 | 7/2003 | Sarchese et al. |
| 2003/0201225 A1 | 10/2003 | Josse et al. |
| 2004/0195954 A1 | 10/2004 | Pirovic |
| 2004/0232358 A1 | 11/2004 | Moruzzi |
| 2005/0224335 A1 | 10/2005 | Carmignani et al. |
| 2007/0007121 A1 | 1/2007 | Guo et al. |
| 2007/0284315 A1 * | 12/2007 | Collins et al. ................. 210/748 |
| 2007/0295012 A1 * | 12/2007 | Ho et al. ........................... 62/56 |
| 2008/0131337 A1 * | 6/2008 | Lucas et al. ................ 422/186.3 |
| 2009/0098014 A1 | 4/2009 | Longstaff |

FOREIGN PATENT DOCUMENTS

| | | |
|---|---|---|
| DE | 3933619 A | 4/1991 |
| EP | 0893411 | 1/1999 |
| GB | 1371099 A | 10/1974 |
| GB | 1482950 A | 8/1977 |
| GB | 2048589 A | 12/1980 |
| GB | 2284091 A | 5/1995 |
| GB | 2307097 A | 5/1997 |
| GB | 2413005 | 10/2005 |
| JP | 61046290 | 3/1986 |
| JP | 61208743 | 9/1986 |
| JP | 3052688 | 3/1991 |
| WO | 9609842 | 4/1996 |
| WO | 9611879 A1 | 4/1996 |
| WO | 9628840 | 9/1996 |
| WO | 9936940 A | 7/1999 |
| WO | 0032244 A | 6/2000 |
| WO | 0109924 A | 2/2001 |
| WO | 03021632 A2 | 3/2003 |

* cited by examiner

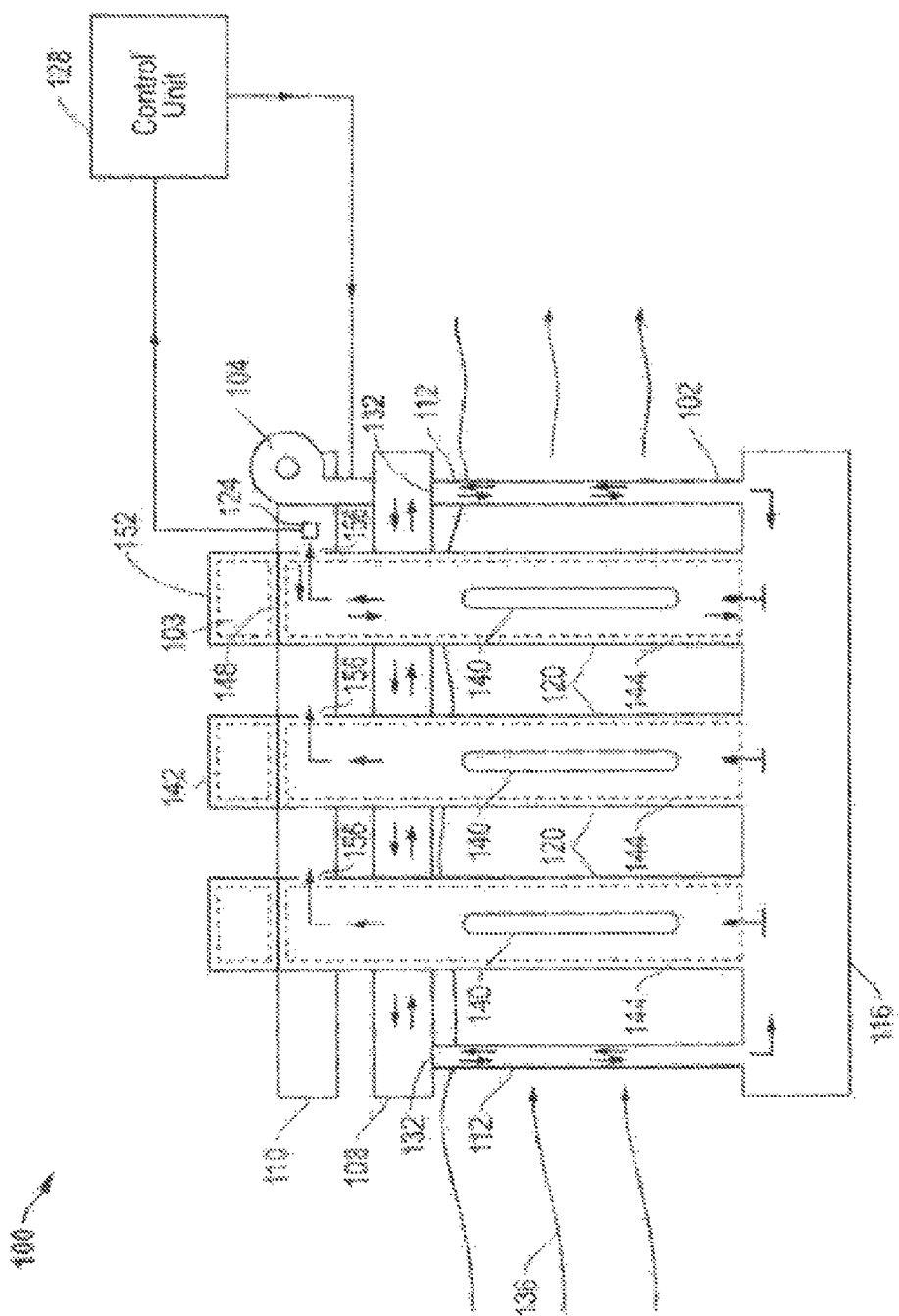

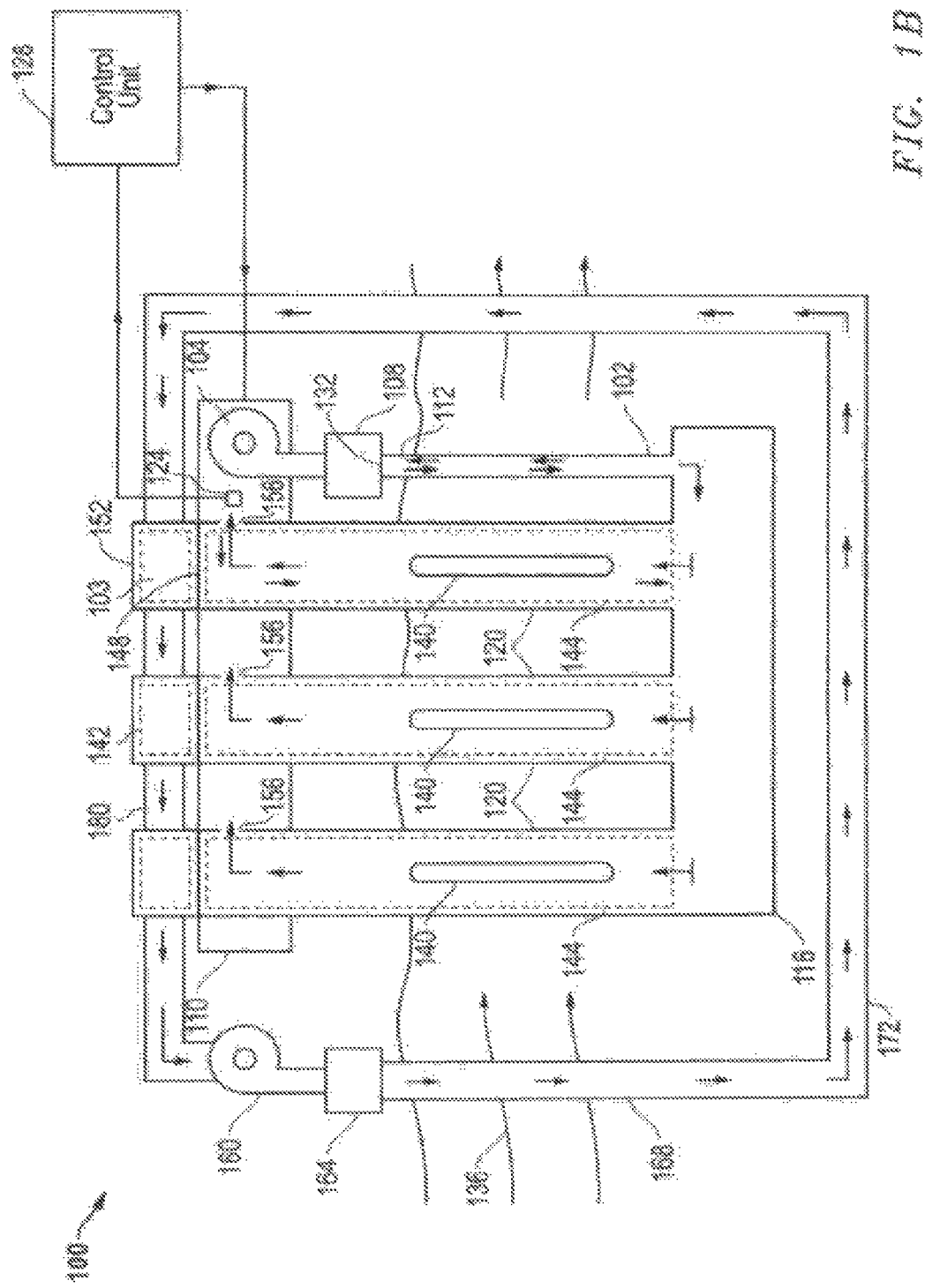

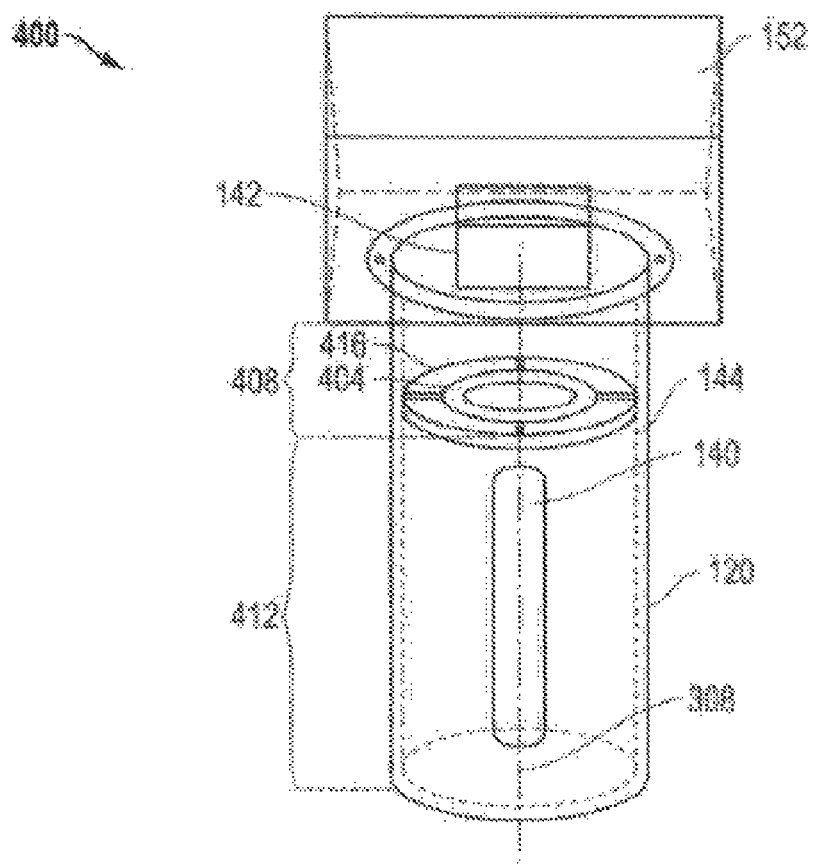
FIG. 4A
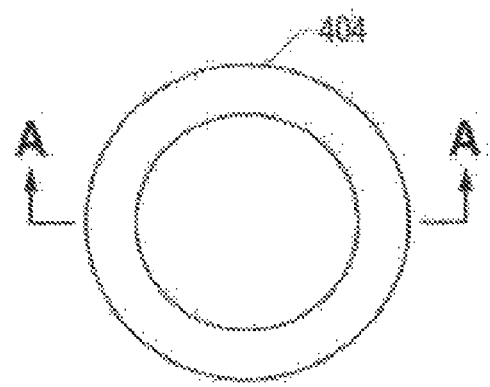
FIG. 4B

METHOD AND SYSTEM FOR ACHIEVING OPTIMAL UV WATER DISINFECTION

FIELD OF THE INVENTION

The present invention is in the field of water disinfection apparatus, in which water to be disinfected or sterilized flows past an ultraviolet (UV) light source.

BACKGROUND

The electric power applied to energize mercury lamps in water treatment systems is converted into heat and ultraviolet (UV or germicidal UVC) light. The heat generated impacts the performance of the water treatment system by reducing the UV output. Current water treatment systems use a system of importing ambient air through a filter; the air passes the lamps and forces excess hot air through air vents. Since the temperature of ambient air may change over a large range, the UV output of the water treatment systems may be affected significantly.

Current water treatment systems employ microwave energy to excite the source of UV radiation. One problem with such systems is that it is difficult to efficiently provide sufficient excitation energy to the UV source and it is also difficult to effectively transfer that energy to the water to be treated. It is, therefore, difficult to arrange apparatus for high throughput industrial water treatment purposes.

SUMMARY

One or more embodiments of the present invention may be used to enhance UV water disinfection by controlling the temperature of the UV light source and adjusting for impedance mismatch of a microwave generator assembly feeding the UV light source.

The UV light source may comprise an ultraviolet lamp module which is at least partially submerged within flowing water to be treated. In one embodiment, the ultraviolet lamp module is vertically oriented in a channel, which, in use, defines the flow of water to be treated. However, the ultraviolet lamp module may, in other embodiments, be oriented in other planes and/or disposed in a chamber. The ultraviolet lamp module further comprises a plurality of lamps arranged in a staggered manner. In moving fluids, energy may be dissipated due to friction and turbulence. This dissipation of energy is called head loss. By staggering the lamps, head loss may be reduced, and mixing of the ultraviolet radiation with the water to be disinfected may be improved. Each of the ultraviolet lamps may further comprise one or more ultraviolet lamp bulbs (also referred herein as ultraviolet bulbs); one or more microwave generator assemblies, each microwave generator assembly comprising a microwave generator; a circular waveguide enclosing the one or more ultraviolet lamp bulbs, and an outer quartz tube enclosing the circular waveguide and ultraviolet lamp bulbs.

Each microwave generator assembly further comprises a power supply, a magnetron, a cooling system utilizing water or air, a transition to a rectangular waveguide, where the rectangular waveguide functions as a transmission line for the microwave, protective means such as thermal cutouts, and a housing enclosing the components. The microwave generator assembly may be disposed above the outer quartz tubes.

The circular waveguide is microwave-opaque and has a shape and size that wholly surrounds the one or more ultraviolet lamp bulbs so as to substantially contain the microwaves within the waveguide. The circular waveguide is made of an electrically conductive mesh having perforations smaller than the size of microwave wavelengths to substantially reduce microwave leakage.

The microwave generator provides microwave energy to excite the ultraviolet bulb. The ultraviolet bulbs emit ultraviolet radiation, at or near the germicidal wavelength of 253.7 nm, which radiates out through the ultraviolet lamp unit to irradiate, and thereby disinfect, the water in the channel.

One or more embodiments of the present invention generally comprise a lamp temperature control system and means for adjusting a microwave impedance mismatch.

Embodiments of the temperature control system generally comprise a recirculating fan, an air supply plenum, a heat exchange unit submerged in the body of water being disinfected, a collector plenum, a hot air collector plenum, and a programmable control unit.

A desired operating temperature of the ultraviolet lamp bulbs is used as the input for a programmable control unit of the temperature control system.

The recirculating fan forces air through the heat exchanger via the air supply plenum. The air supply plenum may be adapted to store a fixed volume of air. As the air flows through the heat exchange unit, it is cooled by the flowing water in contact with the tubes of the heat exchange unit. The cooled air feeds into the collector plenum and is subsequently distributed to the outer quartz tubes enclosing the ultraviolet lamp bulbs. The air cools the ultraviolet lamp bulbs as it flows through the quartz tubes. Upon exiting the quartz tubes, the air temperature is measured and this information is transmitted to the programmable control unit. The programmable control unit stores and analyzes this information, and based on the analysis, determines the deviation of the measured temperature from the desired temperature, and makes adjustments to a rate and/or volume of air flowing through the heat exchange unit. The analysis and determination of the deviation may be automated.

In one embodiment, the programmable control unit may adjust the recirculating fan speed to reduce the determined deviation. In another embodiment, the programmable control unit reduces the determined deviation by throttling the air inlets of the tubes of the heal exchanger by using a motor-driven mechanical damper.

One or more embodiments of the means for adjusting the microwave impedance mismatch generally comprise impedance matching devices such as a matching block or a matching ring or both.

Microwave energy travels from the microwave generator into a rectangular waveguide, to the ultraviolet bulbs, via a circular waveguide. This transition from rectangular to circular waveguides creates an impedance mismatch, which reduces the efficiency of the microwave energy transfer. To adjust for this impedance mismatch, an embodiment of the present invention may comprise a matching block. The matching block is generally disposed at a plane intersecting the direction of travel of the microwave energy as it transitions from the rectangular waveguide to the circular waveguide.

Another microwave impedance mismatch occurs between a first portion and a second portion of the circular waveguide, due to the transition of the microwave energy from traveling through the completely hollow portion of the circular waveguide immediately after exiting the microwave generator to traveling through the portion of the circular waveguide containing the ultraviolet lamp bulb. This impedance mismatch creates a disruption that negatively impacts the efficiency of the microwave energy transfer to the ultraviolet lamp bulb. To adjust for the impedance mismatch, a matching ring is utilized. The matching ring may influence the microwave field in such a way as to reduce the disruption caused by the impedance mismatch.

In yet another embodiment, the present invention may comprise both a matching block and a matching ring to adjust for the two impedance mismatches described above.

Embodiments of the temperature control system and the means for controlling microwave impedance mismatch described herein may be used to achieve optimal UV water disinfection by controlling certain aspects of its involved processes.

These and other embodiments of the invention are described in detail with reference to the following drawings.

BRIEF DESCRIPTION OF THE DRAWINGS

FIGS. 1a and 1b show perspective views of water disinfection apparatus according to certain embodiments of the present invention.

FIG. 4a is a perspective view of a means for adjusting a microwave impedance mismatch having a matching ring according to one embodiment of the present invention.

FIG. 4b shows a top view and a section view of a matching ring according to one embodiment of the present invention.

DETAILED DESCRIPTION OF THE INVENTION

Figure 2A:
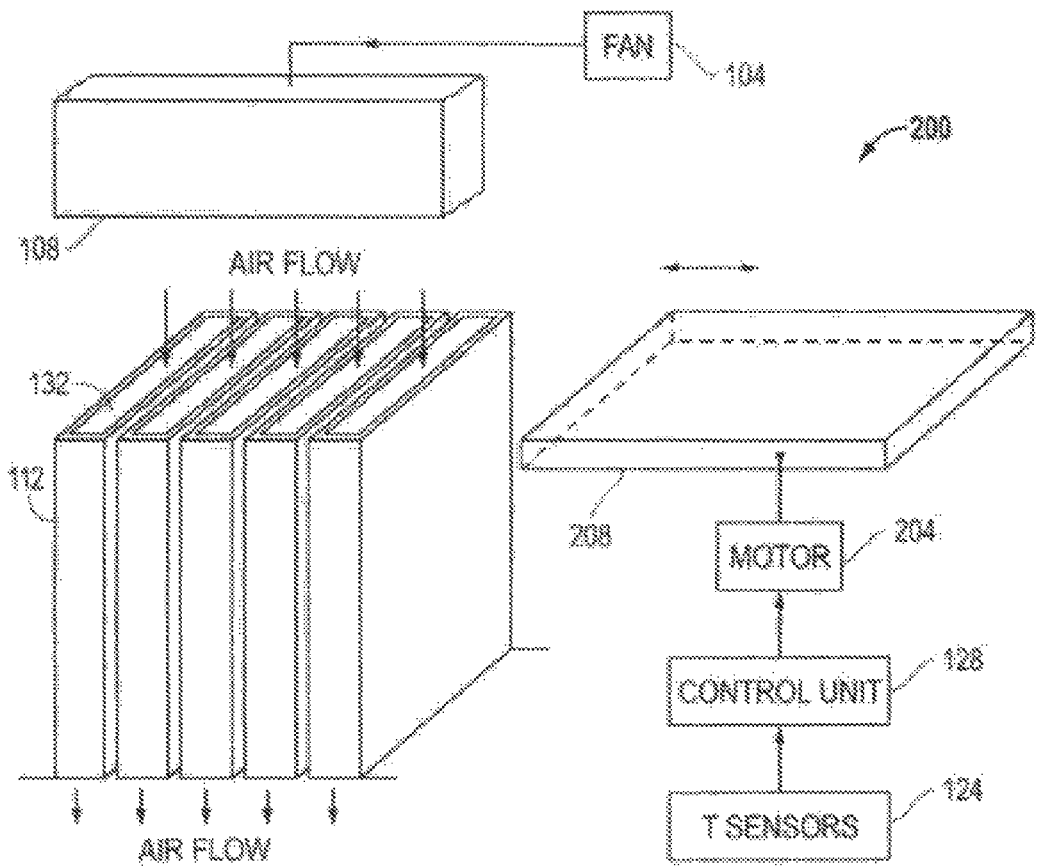
FIGS. 2a and 2b show perspective views of a throttle mechanism according one embodiment of the present invention.

FIG. 1a depicts an exemplary water disinfection apparatus 100 comprising a closed-loop temperature control system 102 and an ultraviolet lamp module 103. The temperature control system 102 comprises a recirculating fan 104, an air supply plenum 108, a plurality of heat exchange tubes 112, an air collector plenum 116, a hot air collector plenum 110, at least one temperature sensor 124, and a programmable control unit 128. The ultraviolet lamp module 103 comprises a plurality of lamps, each lamp having one or more ultraviolet lamp bulbs 140; one or more microwave generators 152, the microwave generators 152 feeding a rectangular waveguide 142; a circular waveguide 144 enclosing the one or more ultraviolet lamp bulbs 140; and an outer quartz tube 120 enclosing the circular waveguide 144 and ultraviolet lamp bulbs 140. The ultraviolet lamp module 103 preferably comprises between 2 to 8 lamps.

The recirculating fan 104 may be attached to the supply plenum 108. The recirculating fan 104 forces air from the supply plenum 108 into the plurality of heat exchange tubes 112. The plurality of heat exchange tubes 112 may be arranged in a linear array substantially perpendicular to a linear array of quartz tubes 120. In some embodiments, the heat exchange tubes 112 may comprise two sets of linear arrays substantially parallel to each other and perpendicular to the linear array of quartz tubes 120. In this embodiment, the two linear arrays of heat exchange tubes 112 are disposed at opposite ends of the linear array of quartz tubes 120. In one embodiment, only one of the two linear arrays of heat exchange tubes 112 is a component of the temperature control system 102. The linear array of heat exchange tubes 112 that is not a component of the temperature control system 102 may regulate the temperature of another aspect of the water disinfection apparatus 100. For example, the linear array of the heat exchange tubes 112 that is not a component of the temperature control system 102 may be used to cool the microwave generators.

In one embodiment, the linear array of heat exchange tubes 112 used in the temperature control system 102 comprises 16 heat exchange tubes 112. In another aspect, the heat exchange tubes 112 are made of stainless steel grade 316. However, the number of heat exchange tubes and the material used to manufacture them may vary in other embodiments. The recirculating fan 104 forces air through the air inlets 132 of the plurality of heat exchange tubes 112 via the supply plenum 108.

The forced air travels through the heat exchange tubes 112, which are at least partially submerged in flowing water 136. The air may flow in either longitudinal direction of the heat exchange tubes 112. Contact between the outer surfaces of the heat exchange tubes 112 and the flowing water 136 causes heat transfer as the temperature of the air inside the heat exchange tubes 112 and the temperature of the flowing water 136 approach thermal equilibrium. Here, the air entering the heat exchange tubes 112 generally has a higher temperature than that of the flowing water 136 in contact with the outer surfaces of the heat exchange tubes 112. Thus, heat from the air is transferred to the flowing water 136 as the air passes through the heat exchange tubes 112, and the air is cooled.

The cooled air exits the heat exchange tubes 112 and feeds into the collector plenum 116. The collector plenum 116 is a reservoir attached to the bottom of at least one quartz tube 120. The collector plenum 116 acts to distribute the air received from the heat exchange tubes 112 into the at least one quartz tube 120.

As the air passes through the quartz tubes 120, heat is transferred from the ultraviolet lamp bulbs 140 to the air, thereby cooling the ultraviolet lamp bulbs 140.

The water disinfection apparatus 100 may comprise a plurality of cylindrical quartz tubes 120, each defining an elongate axis, arranged in a side-by-side array. Each quartz tube 120 may be made of an ultraviolet transparent quartz glass, and acts as a housing for an ultraviolet lamp bulb 140 and a circular waveguide 144. The waveguide 144 is an electrically conductive mesh cylinder that surrounds the ultraviolet lamp bulb 140. The upper end 148 of the quartz tube 120 is disposed at a transition from a rectangular waveguide 142, fed by the microwave generator 152, to a circular waveguide 144. Microwave energy from the microwave generator 152 is directed to the ultraviolet lamp bulb 140, guided via the circular waveguide 144. The ultraviolet lamp bulb 140, excited by the microwave energy, emits ultraviolet radiation, which radiates out through the quartz tube 120 to irradiate, and hence disinfect, the water 136 flowing past.

The air is exhausted proximate the upper end 148 of the quartz tube 120 through air outlet 156 and feeds into the hot air collector plenum 110, which directs the hot air back to the recirculating fan 104. A temperature sensor 124 disposed upstream of the recirculating fan 104 inlet(s) measures the temperature of the air exiting the air outlet 156. In one embodiment, a 3 wire RTD may be used as the temperature sensor to obtain a measurement.

The measurement obtained by the temperature sensor 124 is the feedback signal of the temperature control system 102, and is fed to the programmable control unit 128. The programmable control unit 128 determines the difference between the input signal, which is the desired "setpoint" temperature of the quartz tube 120, and the feedback signal, the difference being the error. The programmable control unit 128 reduces the error to bring the output of the temperature control system 102 to the setpoint temperature. By this means, a constant ultraviolet lamp bulb 140 temperature can be maintained.

The system described is a sealed, fixed-volume, closed-circuit system. Thus, air is recycled through the water disinfection apparatus 100. Because the water disinfection apparatus 100 does not introduce new air from the atmosphere to replenish the system, no air filters are necessary. As the hot air exits the air outlet 156, it enters the hot air collector plenum 110, from where it is directed to the recirculating fan 104 inlet(s) and forced by the recirculating fan 104 through the air supply plenum 108 into the heat exchange tubes 112, thereby beginning a new cycle.

In one embodiment of the temperature control system 102, the programmable control unit 128, upon determining an error, adjusts the speed of the recirculating fan 104 to affect the rate at which air is forced through the heat exchange tubes 112. In one embodiment, the programmable control unit 128 comprises a three-term process controller that may be used to control the recirculating fan speed electronically with a variable speed motor driver interface. A low recirculating fan speed corresponds with a low rate at which air passes through the heat exchange tubes 112. The longer the air takes to flow through the heat exchange tubes 112, the more time it may have to transfer heat to the cooler, flowing water 136 in contact with the outer surfaces of the heat exchange tubes 112.

FIG. 1b depicts another embodiment of the temperature control system 102 having a first set of heat exchange tubes 112 for maintaining a stable ultraviolet lamp bulb 140 temperature as previously described in relation to FIG. 1a and a second set of heat exchange tubes 168 in a sealed, closed-circuit system for cooling the microwave generators 152. A second recirculating fan 160 forces air through the second set of heat exchange tubes 168 via a second supply plenum 164. As the air flows through the second set of heat exchange tubes 168, heat is dissipated from the air to the flowing water in contact with the outer surfaces of the second set of heat exchange tubes 168, thereby cooling the air. The cool air exits the second set of heat exchange tubes 168 and enters a cool air return plenum 172, which transports the cool air to a hood 180 containing the microwave generators 152. The microwave generators 152 dissipate heat to the cool air, thereby cooling the microwave generators 152 and heating the air. The hot air is returned to the second recirculating fan 160, thereby beginning a new cycle.

Figure 2B:
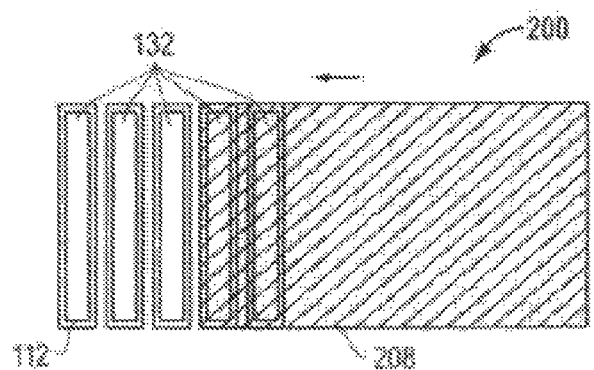

In another embodiment of the temperature control system 102, the rate at which air in the heat exchange tubes 112 loses heat to the flowing water 136 is affected by throttling the air inlets 132 of the heat exchange tubes 112, as shown by FIGS. 2a and 2b. The programmable control unit 128, adjusting for error, determined as previously described, controls a throttle mechanism 200, comprising a motor 204 that drives a mechanical damper 208 over and across the air inlets 132 of the heat exchange tubes 112. The mechanical damper 208 may be a plate having a width and a length sufficient to effectively obstruct air from flowing into the air inlets 132 of heat exchange tubes 112. In one aspect, the mechanical damper 208 is made of stainless steel. In other aspects, the mechanical damper 208 may be made of, for example, aluminum, ultra-high-molecular-weight polyethylene (UHMW), or any other material suitable to restrict the air flow from the recirculating fan 104 to the air inlets 132 of the heat exchange tubes 112. In some embodiments, the face of the mechanical damper 208 restricting the air flow may have dimensions of 60×550 mm.

The motor 204 drives the mechanical damper 208 to progressively cover the air inlets 132 of the heat exchange tubes 112, thereby reducing the number of heat exchange tubes 112 through which air may flow. Thus, similar to varying the recirculating fan speed, the temperature control system 102 may throttle the air inlets 132 of the heat exchange tubes 112 to regulate the heat transfer occurring within the heat exchange tubes 112 and effectively maintain a constant temperature of the ultraviolet lamp bulbs 140 within the quartz tubes 120.

On the first power-up of the temperature control system 102, the mechanical damper 208 is disposed at an arbitrary position proximate the air inlets 132 of the heat exchange tubes 112. The programmable control unit 128 may generate a signal that drives the mechanical damper 208 over the air inlets 132 of the heat exchange tubes 112, progressively covering them and restricting air flow through the heat exchange tubes 112, until the setpoint temperature is reached. Once the setpoint temperature is reached, the position of the mechanical damper 208 will be continuously controlled by the programmable control unit 128 to maintain the setpoint temperature. If power to the temperature control system 102 is interrupted the position of the mechanical damper 208 will be retained until power is resumed.

Temperature sensors (not shown) may be disposed proximate the air inlets 132 of the heat exchange tubes 112 rather than at the air outlets 156 of the quartz tubes 120. Thus, the temperature control system 102 receives a feedback signal of a temperature measurement before the air flows through the heat exchange tubes 112.

In yet another embodiment, the temperature control system 102 is an open-loop control system, wherein the programmable control unit 128 does not receive a feedback signal corresponding with a temperature measurement, and thus does not make adjustments to account for deviations from the desired temperature.

Figure 3A:
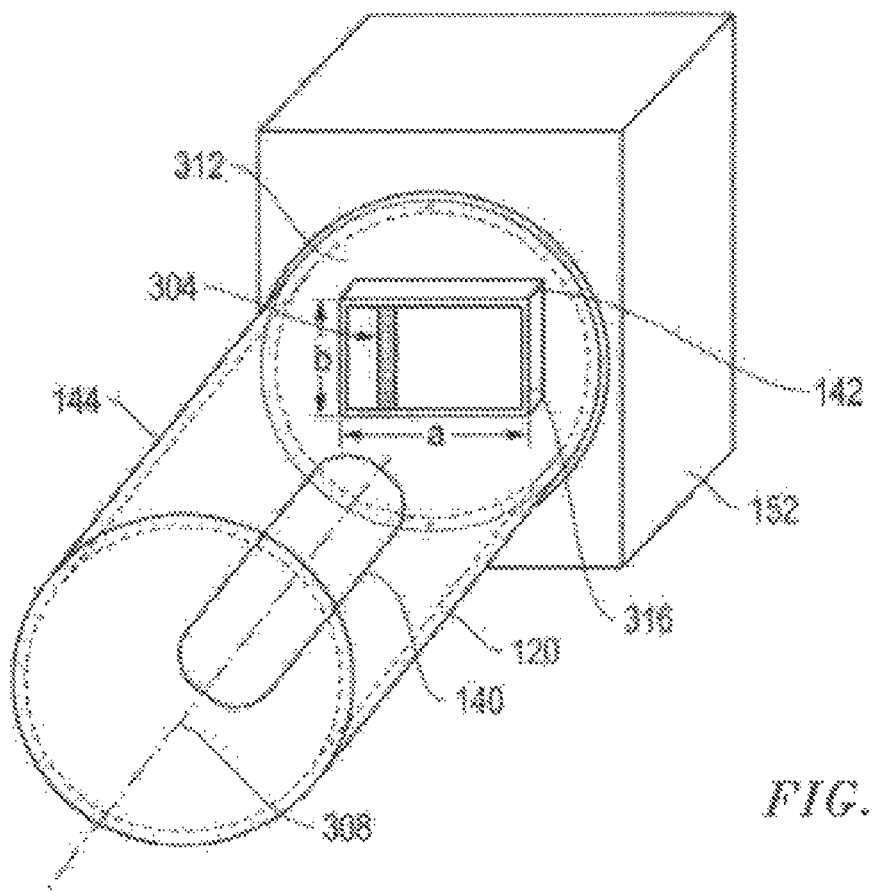
FIG. 3a is a perspective view of a means for adjusting a microwave impedance mismatch having a matching block according to one embodiment of the present invention.

Referring now to FIG. 3a, a means for adjusting microwave impedance mismatch 300 comprises a matching block 304. The ultraviolet light source comprises an elongate quartz tube 120 enclosing at least one ultraviolet lamp bulb 140 and defining an elongate lamp axis 308; and a microwave, generator 152 for exciting the at least one ultraviolet lamp bulb 140.

The microwave generator 152 provides microwave energy to excite the ultraviolet lamp bulb 140. Suitably, the microwave generator 152 comprises a magnetron or other suitable microwave producing device.

Microwave energy travels from the microwave generator 152 into a rectangular TE10 waveguide mode 142. The waves then transition into an operating TE11 circular waveguide mode 144 toward the ultraviolet lamp bulb 140. Such a transition from a rectangular TE10 waveguide mode 142 to a circular TE11 waveguide mode 144 creates a microwave impedance mismatch, negatively impacting the efficiency of microwave energy transfer, and thus, negatively impacting the overall efficiency of the water disinfection apparatus 100.

Figure 3B:
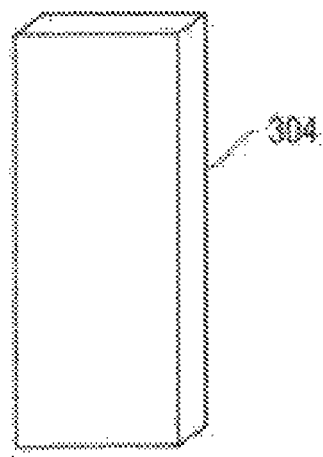
FIG. 3b is a perspective view of a matching block according to one embodiment of the present invention.

The matching block 304 may be a rectangular-shaped plate, as illustrated in FIG. 3b, and acts as a matching device allowing a direct and immediate cross section change from rectangular TE10 142 to circular TE11 144 waveguide modes. The matching block 304 is disposed at the end of the rectangular TE10 waveguide 312 and its length is approximately or less than a quarter of the mode wavelength. In one embodiment, there is one matching block 304 for every microwave generator 152. In other embodiments, more than one matching block 304 per microwave generator 152 may be used.

In one aspect of the present invention, the matching block 304 is made of aluminum. However, in other embodiments, the matching block 304 may be made of another type of metal or carbon.

The longitudinal ends 320 of the matching block 304 may be attached to the sides of the rectangular waveguide 316 having the major 'a' dimension, as illustrated in FIG. 3*a*. The matching block 304 may be disposed at a short distance away from a side of the rectangular waveguide 316 having the 'b' dimension, as illustrated in FIG. 3*a*. In one embodiment, the matching block is disposed at a distance of less than 'a'/2 away from the 'b' side. The matching block 304 is typically shorter than a quarter mode wavelength. In a standard WR340 (43×86 mm) waveguide in the 2450 MHz ISM band, the quarter mode wavelength is approximately 43 mm. In one embodiment, the matching block 304 is square shaped.

The matching block 304 may be affixed to the end of the rectangular TE10 waveguide 312 by either capacitive or direct contact. In one embodiment, the matching block 304 may be affixed to the end of the rectangular TE10 waveguide 312 by using a special high temperature aluminum tape, which is then a capacitive contact with such a small gap that the microwave impedance is in practice a short-circuit. In another embodiment, the matching block 304 may be welded to the end of the rectangular TE10 waveguide 312.

A method of determining an appropriate position of the matching block 304 involves a person skilled in the art first using microwave modeling software to determine the microwave impedance mismatch of the rectangular TE10 waveguide 142 to circular TE11 waveguide 144 transition without a matching block 304. A matching block 304 having a longitudinal length of approximately a quarter TE10 mode wavelength (43 mm) is then introduced to the end of the rectangular TE10 waveguide 312 at a distance of approximately 2 to 3 mm from a side having a 'b' dimension. The microwave modeling software is then run again in order to determine the microwave impedance mismatch of the rectangular TE10 waveguide 142 to circular TE11 waveguide 144 transition with the matching block 304. The first impedance mismatch of the transition without the matching block 304 is compared to the second impedance mismatch of the transition with the matching block 304 to deduce whether or not the impedance mismatch is improving. The matching block 304 is iteratively repositioned at various distances away from the 'b' side. After each repositioning, the modeling software is used to determine whether the impedance mismatch is improved, in this manner, an optimal position for the matching block 304 is determined.

FIG. 4*a* illustrates another embodiment of a means for adjusting microwave impedance mismatching 400 comprising a matching ring 404. The ultraviolet light source comprises an elongate quartz tube 120 enclosing at least one ultraviolet lamp bulb 140 and defining an elongate lamp axis 308; and a microwave generator 152 for exciting the at least one ultraviolet lamp bulb 140.

The distance between the magnetron's antenna (not shown) and the ultraviolet lamp bulb 140 is performance-sensitive as the microwave field is typically disrupted when it reaches the ultraviolet lamp bulb 140. The disruption is caused by an impedance mismatch between two portions, a first portion 408 and a second portion 412, of the circular TE11 waveguide 144 previously described in relation to FIG. 1*a*. The first portion 408 of the circular TE11 waveguide 144 is defined as the portion through which the microwave energy travels before reaching the ultraviolet lamp bulb 140. The second portion 412 of the circular TE11 waveguide 144 is defined as the subsequent portion containing the ultraviolet light bulb 140. This disruption reflects microwave energy back to the microwave generator 152, reducing the efficiency of microwave energy transfer, and thus, reducing the overall efficiency of the water disinfection apparatus 100.

The matching ring 404 may be an annular-shaped matching reactance element, as illustrated in FIG. 4*b*, disposed inside the elongate lamp tube 120 and may be incorporated into the top of the lamp cassette 416, the axis of the matching ring 404 coincident with the elongate lamp axis 308.

In one embodiment, the matching ring 404 may be made of pure aluminum. In another embodiment, the matching ring 404 may be made of nickel-plated brass. Other embodiments of the matching ring 404, however, may be made of any other material of low resistivity suitable for improving the impedance mismatch described above, without resulting in significant self-heating by the microwave currents in it.

The distance of the matching ring 404 from the ultraviolet lamp bulb 140 and the dimensions of the matching ring 404 are two parameters that may influence the microwave field in such a way as to reduce disruption. These parameters are determined on a load-by-load basis. Different types of ultraviolet lamp bulbs 140 may require different values for these parameters. The matching ring 404 may be disposed less than a quarter free space wavelength above the top of the crown of the ultraviolet lamp bulb 140. In one embodiment, the matching ring 404 may be disposed approximately 6 mm above the top of the crown of the ultraviolet lamp bulb 140. The inner diameter of the matching ring 404 may range from approximately 20 mm to 40 mm. In a preferred embodiment, the matching ring 404 may have an inner diameter of 28 mm and a square cross section having dimensions of 1.5×1.5 mm. In yet another embodiment, the matching ring 404 has a round cross section. The distance of the matching ring 404 from the ultraviolet lamp bulb 140 and the dimensions of the matching ring 404 may vary in other embodiments.

A method of determining an appropriate position of the matching ring 404 involves a person skilled in the art first using microwave modeling software to determine the microwave impedance mismatch of the transition between the first portion 408 and the second portion 412 of the circular TE11 waveguide 144 without a matching ring 404. A matching ring 404 is introduced into the circular TE11 waveguide 144 above and proximate to the ultraviolet lamp bulb 140. The microwave modeling software is then run again in order to determine the microwave impedance mismatch with the inclusion of the matching ring 404. The first impedance mismatch of the transition without the matching ring 404 is compared to the second impedance mismatch of the transition with the matching ring 404 to deduce whether or not the impedance mismatch is improving. The matching ring 404 is iteratively repositioned at various distances away from the ultraviolet lamp bulb 140. After each repositioning, the modeling software is used to determine whether the impedance mismatch is improved. In this manner, actual experiments with microwave power in a test set-up are conducted for verification and possible fine adjustments allow for the determination of an optimal position for the matching ring 404.

Figure 5:
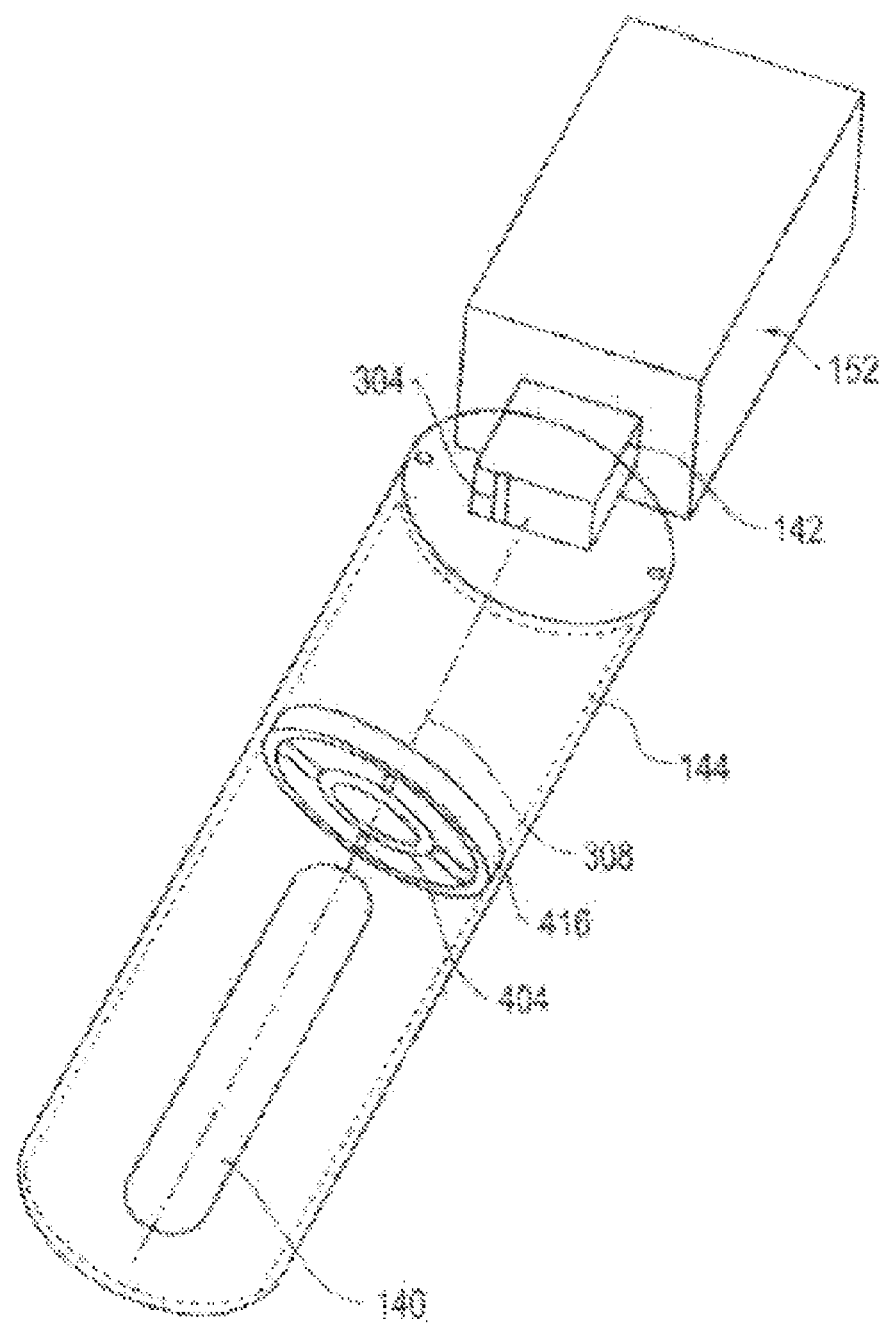
FIG. 5 is a perspective view of a means for adjusting a microwave impedance mismatch having a matching block and a matching ring according to one embodiment of the present invention.

In yet another embodiment, the present invention may comprise both a matching block 304 and a matching ring 404, as illustrated in FIG. 5, to adjust for the two impedance mismatches described above.

In particular embodiments, the temperature control system and the means for adjusting the impedance mismatch may be combined. The means for adjusting the impedance mismatch may comprise a matching block or a matching ring or both.

The use of the word "exemplary" in this disclosure is intended to mean that the embodiment or element so described serves as an example, instance, or illustration, and is not necessarily to be construed as preferred or advantageous over other embodiments or elements. The description of the various exemplary embodiments provided above is illustrative in nature and is not intended to limit the invention, its application, or uses. Thus, variations that do not depart from the gist of the invention are intended to be within the scope of the embodiments of the present invention. Such variations are not to be regarded as a departure from the spirit and scope of the present invention.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

What is claimed is:

1. A method for enhancing the ultraviolet output of a water disinfection apparatus, the method comprising:
    maintaining one or more ultraviolet (UV) light sources at a stable operating temperature; and
    adjusting for an impedance mismatch between a microwave generator assembly and the UV light source to which the microwave generator assembly feeds microwave energy, wherein the UV light source comprises:
        a UV lamp module at least partially submerged in water to be disinfected, the UV lamp module comprising a plurality of UV lamps, each lamp further comprising one or more UV bulbs;
        the microwave generator assembly further comprising one or more microwave generators for converting electrical power into the microwave energy, the microwave energy transitioning from the microwave generators into one or more rectangular waveguides;
        one or more optically transparent circular waveguides for guiding the microwave energy to the one or more UV bulbs, the circular waveguide enclosing the one or more UV bulbs, the circular waveguide further comprising a mesh having intersecting filaments, the circular waveguide essentially transparent to UV radiation and substantially opaque to microwaves, wherein the microwave energy further transitioning from the rectangular waveguide to the circular waveguide; and
        an outer quartz tube enclosing the circular waveguide and the UV bulbs,
            the maintaining the one or more UV light sources at a stable operating temperature further comprises:
            providing a temperature control system, the temperature control system comprising a sealed air cooling system impervious to ambient air, the temperature control system further comprising:
                an upper air supply plenum;
                a recirculating fan positioned on the upper air supply plenum;
                a heat exchange unit at least partially immersed in the water to be disinfected, the heat exchange unit further comprising one or more heat exchange tubes, each heat exchange tube having an air inlet for receiving the air from the air supply plenum;
                a lower air collector plenum for receiving the air from the heat exchange tubes and supplying the air to the outer quartz tube, the lamps disposed between the upper air supply plenum and the lower air collector plenum;
                a hot air collector plenum for receiving the air from the quartz tube, the hot air collector plenum transporting the air back to the recirculating fan; and
                a programmable control unit for maintaining a desired air temperature measurement, the desired air temperature measurement corresponding to the stable operating temperature of the UV light source, and facilitating heat dissipation in the heat exchange unit, wherein heat is transferred from the air in the heat exchange tube into the water until a thermal equilibrium is approached.

2. The method of claim 1, further facilitating cooling of the UV bulbs by transferring heat from the UV bulbs to the air circulating through the outer quartz tube.

3. The method of claim 1, further comprising measuring a temperature of the air exiting the outer quartz tubes and providing the measured air temperature as a feedback signal to the programmable control unit.

4. The method of claim 3, further comprising calculating a difference between the feedback signal and the desired air temperature measurement for determining an error measurement, the error measurement substantially reduced by the programmable control unit by ensuring the feedback signal approximates the desired air temperature measurement.

5. The method of claim 4, the ensuring the feedback signal approximates the desired air temperature measurement further comprising regulating a flow of the air from the air supply plenum to the heat exchange unit.

6. The method of claim 5, the regulating the air flow into the heat exchange unit further comprising:
    forcing the air into heat exchange tubes using the recirculating fan; and
    adjusting a speed of the recirculating fan electronically to ensure the air flows through the heat exchange tubes at a desired rate and for a desired duration, wherein a longer flow duration corresponds to an increased time available for the heat dissipation.

7. The method of claim 5, the regulating the air flow into the heat exchange unit further comprising:
    controlling an effective surface area of the heat exchange tubes available for heat dissipation, wherein responsive to a signal from the programmable control unit a mechanical damper covers and/or uncovers each of the inlets of the heat exchange unit until the desired air temperature measurement is reached.

8. The method of claim 1, further comprising arranging the lamps in one or more staggered arrays for reducing head loss and ensuring improved mixing of UV radiation from the UV bulbs with the water to be disinfected.

9. The method of claim 1, the adjusting for the microwave impedance mismatch further comprising facilitating an efficient transfer of microwave energy to the one or more UV bulbs from a rectangular TE10 waveguide mode to a circular TE11 waveguide mode as the microwave energy transitions from the rectangular waveguide to the circular waveguide.

10. The method of claim 9, wherein the adjusting for the microwave impedance mismatch further comprises affixing a matching block at an end of the rectangular waveguide, the matching block facilitating a direct and immediate cross sectional change from the rectangular TE10 waveguide mode to the circular TE11 waveguide mode.

11. The method of claim 10, further comprising determining an appropriate position for affixing the matching block.

12. The method of claim 1, wherein the adjusting for the microwave impedance mismatch further comprising facilitating an efficient transfer of microwave energy to the one or more UV bulbs during a passage of the microwaves between a first portion and a second portion of the circular waveguide, wherein the first portion of the circular waveguide is substantially hollow, and further wherein the UV bulb is enclosed proximate the second portion of the circular waveguide.

13. The method of claim 12, further comprising placing a matching ring inside the lamp, the matching ring positioned at an optimal distance from a crown of the UV bulb to adjust for the microwave impedance mismatch.

14. A system for enhancing the ultraviolet output of a water disinfection apparatus, the system comprising:
one or more ultraviolet (UV) light sources, the UV light source comprising:
a UV lamp module at least partially submerged in water to be disinfected, the UV lamp module comprising a plurality of UV lamps, each lamp further comprising one or more UV bulbs;
a microwave generator assembly comprising one or more microwave generators for converting electrical power into microwave energy, the microwave energy transitioning from the microwave generators into a rectangular waveguide;
one or more optically transparent circular waveguides for guiding the microwave energy to the one or more UV bulbs, the circular waveguide enclosing the one or more ultraviolet bulbs, the circular waveguide further comprising a mesh having intersecting filaments, the circular waveguide essentially transparent to UV radiation and substantially opaque to microwaves, the microwave energy further transitioning from the rectangular waveguide to the circular waveguide;
one or more outer quartz tubes enclosing the circular waveguide and the one or more UV bulbs;
a temperature control system for maintaining the UV light source at a stable operating temperature, the temperature control system comprising a sealed air cooling system impervious to ambient air, the temperature control system further comprising:
an upper air supply plenum;
a recirculating fan positioned on the upper air supply plenum;
a heat exchange unit at least partially immersed in the water to be disinfected, the first heat exchange unit further comprising one or more heat exchange tubes, each heat exchange tube having an air inlet for receiving the air from the air supply plenum;
a lower air collector plenum for receiving the air from the heat exchange tubes and supplying the air to one or more outer quartz tubes, the lamps disposed between the upper air supply plenum and the lower air collector plenum;
a hot air collector plenum for receiving the air from the quartz tube, the hot air collector plenum transporting the air back to the first recirculating fan; and a
a programmable control unit for maintaining a desired lamp temperature,
wherein an outer surface of the heat exchange tubes is at least partially immersed in the channel of water to facilitate heat dissipation through the water, and
means for facilitating an efficient transfer of microwave energy to the UV light source by adjusting for an impedance mismatch of a microwave generator assembly feeding microwave energy to the UV light source.

15. The system of claim 14, further comprising at least one air temperature measurement sensor disposed proximate the outer quartz tube, the sensor providing the measured air temperature as a feedback signal to the programmable control unit.

16. The system of claim 15, further comprising means for calculating a difference between the feedback signal and a pre-determined desired air temperature measurement, the difference determining an error measurement.

17. The system of claim 16, further comprising means for substantially reducing the error measurement by ensuring the feedback signal approximates the desired air temperature measurement.

18. The system of claim 14, further comprising electronic means for adjusting the speed of the recirculating fan to ensure the fixed volume of air flows through the heat exchange tubes at a desired rate and for a desired duration, wherein a longer flow duration corresponds to an increased time available for heat dissipation.

19. The system of claim 14, further comprising a throttle system, the throttle system comprising:
a mechanical damper unit, the mechanical damper unit comprising a plate having a width and length for substantially completely blocking the air flow into the inlets of the heat exchange tubes; and
a motor driving unit for driving the mechanical damper unit over and across the inlets of the heat exchange tubes.

20. The system of claim 19, further comprising means for controlling an effective surface area of the heat exchange tubes available for heat dissipation, wherein in response to a signal from the programmable control unit, the mechanical damper covers and/or uncovers each of the air inlets of the heat exchange unit until the desired air temperature measurement is reached.

21. The system of claim 14, the means for adjusting for the microwave impedance mismatch further comprising a matching block, the matching block affixed to an end of the rectangular waveguide.

22. The system of claim 21, the matching block further facilitating an efficient transfer of the microwave energy to the one or more UV bulbs from a rectangular TE10 waveguide mode to a circular TE11 waveguide mode as the microwave energy transitions from the rectangular waveguide to the circular waveguide.

23. The system of claim 21, wherein the matching block having a length shorter than 43 mm.

24. The system of claim 21, further comprising a modeler for modeling an appropriate position for affixing the matching block to the rectangular waveguide.

25. The system of claim 14, the means for adjusting for the microwave impedance mismatch further comprising a matching ring, the matching ring comprising an annular-shaped matching reactance element, the matching ring having an inner diameter between 20 mm-40 mm.

26. The system of claim 25, the matching ring further facilitating an efficient transfer of the microwave energy to the one or more UV bulbs during a passage of the microwaves between a first portion and a second portion of the circular waveguide, the first portion of the circular waveguide is substantially hollow, and the UV bulbs enclosed proximate the second portion of the circular waveguide.

27. The system of claim 25, further comprising positioning the matching ring at an optimal distance from a crown of the UV bulb.

* * * * *